United States Patent [19]

Legrow et al.

[11] Patent Number: 5,679,335

[45] Date of Patent: Oct. 21, 1997

[54] CYCLIC ALKYLMETHYLSILOXANES FOR SKIN CARE

[75] Inventors: Gary Edward Legrow; Regina Marie Malczewski, both of Midland, Mich.

[73] Assignee: Dow Corning Corporation, Midland, Mich.

[21] Appl. No.: 866,392

[22] Filed: Apr. 10, 1992

Related U.S. Application Data

[63] Continuation-in-part of Ser. No. 750,135, Aug. 26, 1991, abandoned.

[51] Int. Cl.$^6$ ............................................. A61K 7/40
[52] U.S. Cl. ........................ 424/78.03; 424/401; 556/460
[58] Field of Search .............................. 424/401, 47, 63, 424/70, 71, 78.02, 78.03; 514/844; 556/450, 460

[56] References Cited

U.S. PATENT DOCUMENTS

| | | | |
|---|---|---|---|
| 4,784,844 | 11/1988 | Thimineur et al. | 424/65 |
| 4,855,129 | 8/1989 | Steinbach et al. | 424/63 X |
| 4,874,868 | 10/1989 | Bolich, Jr. | 556/460 X |
| 4,906,458 | 3/1990 | Shigeta et al. | 424/63 |
| 5,061,482 | 10/1991 | Halloran et al. | 424/71 |
| 5,086,146 | 2/1992 | Liles et al. | 528/15 |

FOREIGN PATENT DOCUMENTS 01294612  11/1989  Japan.

*Primary Examiner*—John C. Bleutge
*Assistant Examiner*—Robert H. Harrison
*Attorney, Agent, or Firm*—Timothy J. Troy

[57] ABSTRACT

A method of treating human skin to decrease transepidermal water loss. A method of enhancing the substantivity of conditioning compounds applied to the skin. A film forming conditioning formulation which includes as an ingredient thereof an organosilicon compound is applied to the skin. The improvement resides in the utilization of a formulation which includes as the organosilicon compound a cyclic alkylmethyl polysiloxane.

18 Claims, No Drawings

CYCLIC ALKYLMETHYLSILOXANES FOR SKIN CARE

This is a continuation-in-part of application Ser. No. 07/750,135, filed Aug. 26, 1991, now abandoned.

BACKGROUND OF THE INVENTION

This invention relates to personal care and to certain alkylmethyl polysiloxanes useful in skin care applications. More particularly the invention is directed to moisturization and to the formation of films on the skin which function as barriers in order to reduce transepidermal water loss with the result that skin is softened by virtue of its own moisture. In a recent publication by Th. Goldschmidt AG dated July 1989 and entitled "ABIL Silicones" it is reported that certain polysiloxane polyalkylene copolymers known as ABIL-WAX 9800 and ABIL-WAX 9801 have utility in skin care applications such as day creams, all purpose creams and body lotions. The materials are said to be soluble in cosmetic oils and waxes and to protect against aqueous media when employed in amounts of one to five percent by weight. These materials otherwise known under The Cosmetics, Toiletries and Fragrances Association adopted names of stearyl dimethicone and cetyl dimethicone have the structural formula:

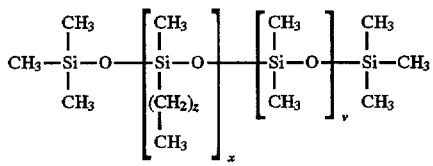

The "ABIL" siloxanes are described as having a linear structure in contrast to the present invention which is in the form of a cyclic structure. Also the "ABIL" wax described by the Goldschmidt reference contains residual metal and is not homogenous. In contrast the present invention is in a homogenous state and does not contain metallic residue which therefore results in a safer and purer product for personal care applications. The cyclic siloxanes of the present invention are more substantive to the skin surface, and form a film on the skin which functions as a barrier to prevent the permeation of moisture upward from the skin and through the film. This reduces the transepidermal water loss from the skin with the result that the skin is softened due to the retention of more of its own moisture. Test data indicate that the cyclic siloxanes of the present invention possess these improved properties to an unexpectedly greater degree than the "ABIL" silicones as will be shown hereinafter.

U.S. Pat. No. 4,574,082 issued Mar. 4, 1986 describes cosmetics containing a dimethylpolysiloxane in admixture with linear organopolysiloxanes such as polymethyloctylsiloxane and polymethyloctadecylsiloxane. There is no disclosure or description of cyclic compositions in the '082 patent. By applying films containing only silicones which are high molecular weight cyclic alkylmethylsiloxanes, it has been possible in accordance with the present invention to reduce substantially transepidermal water loss from the skin and to therefore provide occlusive moisturizing treatments.

Protective skin creams are described in United Kingdom Patent No. 737,134 granted Sep. 21, 1955. These skin creams are said to include certain hydrocarbon substituted organosiloxanes. The hydrocarbon radicals are noted preferably to be lower alkyl radicals such as methyl, ethyl, and propyl however the British patent indicates that for certain uses higher alkyl radicals such as octadecyl and lauryl radicals may be desired. There is no description or disclosure of cyclic materials in the '134 patent. Also the description of the above compositions allows the presence of higher alkyl radicals at the ends of the polymer chain in contrast to the cyclic compositions of the present invention.

Skin care lotions and creams said to include mixed $C_1-C_3$ alkyl polysiloxanes such as methylethylpolysiloxane are disclosed in U.S. Pat. No. 4,960,764 issued Oct. 2, 1990. Siloxanes including short chain alkyl groups such as ethyl and propyl do not differ significantly from dimethylpolysiloxanes and therefore the siloxanes of the '764 patent suffer from the disadvantage of being ineffective moisture barriers as explained above in detail. Thus methylethylpolysiloxane and methylpropylpolysiloxane will each possess a high water permeability through their respective films and will each be incapable of functioning as effective occlusive barriers in comparison to the high molecular weight $C_{12}$ to $C_{30}$ cyclic alkylmethylsiloxanes of the present invention. Further short chain alkylmethylpolysiloxanes as described in the '764 patent are less durable and their films may be easily removed from the surface of the skin in contrast to the substantive nature of the films formed by the cyclic materials of the present invention.

In U.S. Pat. No. 4,784,844 issued Nov. 15, 1988 there are described certain water based emulsions for cosmetic and medicinal application which are said to contain a cyclic polysiloxane of the formula

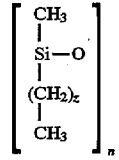

in which n is an integer from three to ten and z is an integer having a value of from one to ten. These cyclic materials are stated to be volatile. In contrast to the '844 patent, the present invention utilizes cyclic alkylmethyl polysiloxanes which are non-volatile and which can be delivered to the skin in the form of an anhydrous medium. In addition, the alkyl group $(CH_2)_zCH_3$ of the '844 is smaller than the corresponding alkyl group of the cyclic alkylmethyl polysiloxanes of the present invention. Thus the alkyl group in the '844 patent varies from $C_2$ to $C_{11}$ whereas the alkyl group of the present invention is $C_{12}$ to $C_{30}$.

In U.S. Pat. No. 5,002,762 issued Mar. 26, 1991 there are described volatile silicon compounds for household and cosmetic applications which are stated to contain a cyclic polysiloxane of the formula

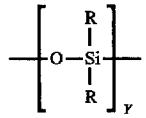

in which Y is an integer from one to four and R can be independently a C1 to C10 alkyl group. These silicon compounds are also stated to be volatile. In contrast to the '762 patent, the present invention utilizes cyclic alkylmethyl polysiloxanes which are non-volatile and which can be delivered to the skin in the form of an anhydrous medium. Also, the alkyl group R of the '762 patent is smaller than the corresponding alkyl group of the cyclic alkylmethyl polysiloxanes of the present invention. The alkyl group of the '762 patent varies from $C_1$ to $C_{10}$ while the alkyl group in the present invention ranges from $C_{12}$ to $C_{30}$.

Accordingly new and novel personal care formulations are provided herein in which a cyclic alkylmethyl polysiloxane is utilized as a substantive barrier to water loss to provide soft skin.

SUMMARY OF THE INVENTION

The invention is directed to a method of treating human skin to decrease transepidermal water loss. The invention is also directed to a method of enhancing the substantivity of conditioning compounds on human skin. A film forming conditioning formulation which includes as an ingredient thereof an organosilicon compound is applied to the skin. The improvement resides in the utilization of a formulation which includes as the organosilicon compound a cyclic alkylmethyl polysiloxane.

The invention is also directed to personal care and to certain cyclic alkylmethyl polysiloxanes useful in skin care applications. Further the invention is related to moisturization and to the formation of films on the skin which function as barriers in order to reduce transepidermal water loss with the result that skin is softened by virtue of its own moisture. In addition the invention includes a method for making the cyclic alkylmethyl polysiloxanes and skin care formulations containing cyclic alkylmethyl polysiloxanes.

These and other features, objects and advantages of the present invention will be apparent upon consideration of the following detailed description of the invention.

DETAILED DESCRIPTION OF THE INVENTION

In order to treat human skin for the purpose of effecting a decrease in the transepidermal water loss, there is applied to the surface of the skin a film forming conditioning formulation which can be anhydrous. The alkylmethyl cyclic polysiloxanes are compounds having the formula

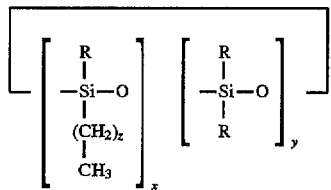
(I)

In the formula x and y are integers the sum of which is four, five, or six provided that x cannot be zero, and z is an integer which has a value of eleven to about twenty-nine. R is an alkyl group having one to six carbon atoms. Typically the R group is methyl although other alkyl radicals may be employed. Thus the most preferred compounds have the formula

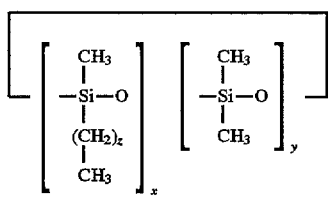
(II)

in which x, y and z are as defined above. Thus where x is one y is three, four, or five; where x is two y is two, three, or four; where x is three y is one, two or three; where x is four y is zero, one, or two; and where x is five y is zero or one.

The cyclic alkylmethylpolysiloxanes can be delivered to the skin as an anhydrous formulation which is applied to the skin in the form of a solution of the cyclic alkylmethyl polysiloxane dissolved in a volatile solvent such as an aliphatic hydrocarbon, aliphatic alcohol, aliphatic ester, or a low viscosity cyclic silicone fluid. Such volatile solvents are described below. The cyclic alkylmethylsiloxanes of the present invention can be delivered to the skin as a hydrous or as an anhydrous formulation.

The cyclic alkylmethyl polysiloxanes of this invention can be produced by the reaction of a linear siloxane having Si—H functionality in the chain such as $(Me_3SiO_{1/2})_2(OSiMeH)_x$ in which Me is methyl and x is forty to about one hundred, and a cyclic siloxane having ($Me_2SiO$) units of the formula $(Me_2SiO)_x$ in which Me is methyl and x is an integer of about three to six preferably four or five. The reaction product is about ninety percent by weight of a linear polymer and ten percent by weight of a cyclic polymer. The reaction product is then contacted with a slight stoichiometric excess of an alkene $CH_2$=CHR in the presence of a platinum on carbon catalyst and a cyclic alkylmethylsiloxane having the structure of formula (II) shown above is produced.

The cyclic alkylmethyl polysiloxanes of this invention can also be produced by the direct hydrolysis of methylhydrogen dichlorosilane to form cyclomethylhydrogen polysiloxanes, or by the direct cohydrolysis of methylhydrogen dichlorosilane and dimethyl dichlorosilane to form cyclomethylhydrogensiloxy dimethylsiloxy copolymers. The reaction product is then contacted with a slight stoichiometric excess of an alkene $CH_2$=CHR in the presence of a platinum on carbon catalyst and a cyclic alkylmethylsiloxane having the structure of formula (II) shown above is produced.

Batch production of the alkylmethyl polysiloxanes is conducted by adding the reaction product to a non-agitated suspension of the catalyst in the alkene at about sixty degrees Centigrade. Continuous production of the alkylmethyl polysiloxanes is conducted by pumping a preheated solution of a five percent stoichiometric excess of an alkene $CH_2$=CHR and the reaction product through a packed column containing platinum on carbon catalyst chips. The column will require provision for the removal of heat because of the exothermic nature of the reaction.

The materials are further processed in accordance with the present invention in order to provide a more cosmetically acceptable product by removing from the product any remaining cyclic siloxane and any residual methylhydrogendimethylsiloxane cocyclics present as $(MeHSiO)(Me_2SiO)_3$. The alkylmethyl polysiloxanes produced in accordance with the present invention have been found to contain at most about 0.5 percent residual alkene and about 99.5 percent alkylmethyl polysiloxane product. No measurable residual amount of platinum has been detected. The products are otherwise colorless, odorless, non-volatile, clear and stable materials. The products are particularly adapted to skin care in that the materials have been found to form films on the skin which possess a very low water vapor permeability enabling the materials to form a barrier on the skin which will reduce moisture loss from the stratum corneum. The alkylmethyl polysiloxanes find utility in skin creams and lotions including facial products such as cleaners and moisturizers, hand creams, baby creams and sun care creams and lotions.

The water content of the outer layers of the stratum corneum of human skin is a controlling factor in the appearance of dry skin symptoms. When the stratum corneum contains an adequate amount of water within the range of ten to twenty percent the skin remains flexible. However when the water content falls below ten percent the stratum corneum often becomes brittle and rough and can exhibit scaling and cracking. The stratum corneum receives its water from the deep layers of the epidermis by diffusion, from ambient air, or when it is brought into direct contact with water. The diffusion process is controlled by the water content of the skin as well as the concentration gradient. In a very dry environment the water loss from the external skin layers can be significant and often exceeds the rate of replacement by diffusion. An occlusive barrier placed onto the surface of the skin acts to retard the water loss to the environment and allows the skin surface to rehydrate by the diffusion process. Due to the effectiveness and safety of the alkylmethyl polysiloxanes they serve as useful skin conditioners, occlusive moisturizers and contribute to dry skin prevention by protection and moisture retention as well as dry skin repair by emolliency, lubricity and moisture restoration.

The cyclic alkylmethylsiloxanes of the present invention are provided in an amount sufficient to provide the desired properties (e.g. occlusivity, substantivity, etc.) to the skin. The total amount of cyclic alkylmethylsiloxane in any formulation will vary depending on the additional components present. Generally, the amount of cyclic alkylmethylsiloxane present will comprise between about 1 and about 90 weight percent of the final formulation.

Volatile solvents which may be employed to deliver the alkylmethyl polysiloxane to the skin include aliphatic hydrocarbons among which are isoparaffins such as a C10-11 Isoparrafin (sold by Exxon as ISOPAR G); aliphatic alcohols such as isopropyl alcohol and ethyl alcohol; aliphatic esters such as isopropyl myristate and ethyl acetate; and volatile siloxanes. The solvent can also be a linear or cyclic polysiloxane. The solvent must be compatible with and capable of dissolving, dispersing, or suspending the alkylmethyl polysiloxane and any optional component which may be present. Volatile siloxanes which may be employed as solvents include the volatile low viscosity cyclic silicone fluids and linear silicones. Representative of these materials are polydimethylcyclosiloxane and hexamethyldisiloxane. Such fluids have viscosities of 0.65 to 5.0 centistokes measured at twenty-five degrees Centigrade. Non-volatile solvents can also be employed in the present invention. Non-volatile oils commonly utilized in cosmetic applications are suitable for use as solvents in the present invention.

The volatile cyclic silicones conform to the formula $(R_2SiO)_x$ in which R is an alkyl radical having from one to three carbon atoms or a phenyl group. Typically the cyclic siloxanes have the formula $[(CH_3)_2SiO]_x$ in which x is an integer from three to ten. Volatile cyclic siloxane compounds found to be especially useful in accordance with the present invention are the tetramer compound octamethylcyclotetrasiloxane and the pentamer compound decamethylcyclopentasiloxane. Mixtures of the tetramer and pentamer may also be employed. Such cyclic siloxanes have viscosities ranging from about 2.5 centistokes to about five centistokes. These materials are also known under The Cosmetics, Toiletries and Fragrance Association designation as cyclomethicone.

Volatile low viscosity linear silicone fluids which may be employed as solvents have the formula $R_3SiO(R_2SiO)_nSiR_3$ in which R is an alkyl radical having one to six carbon atoms and n is an integer of from two to nine. Representative of the linear siloxane is hexamethyldisiloxane of the formula

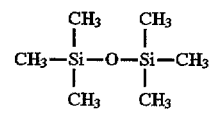

which has a viscosity of 0.65 centistokes measured at twenty-five degrees Centigrade.

The cyclic low viscosity volatile silicones are clear fluids and are essentially odorless, nontoxic, nongreasy and nonstinging. Cosmetically they are nonirritating to the skin and possess the properties of good spreadability and ease of rub-out. The materials evaporate leaving behind no residue.

In addition to the volatile solvent and the cyclic alkylmethyl polysiloxane, skin care formulations in accordance with this invention may optionally contain other emollients, sunscreens, and adjuvants such as perfumes, fragrances and preservatives. Examples of other emollients and moisturizers which may be included in compositions of this invention include straight, branched or cyclic hydroxy compounds such as alcohols containing 1 to 30 carbon atoms; straight, branched or cyclic carboxylic acids containing 1 to 31 carbon atoms; acid esters containing $C_1$ to $C_{30}$ carboxylic acids esterfied with $C_1$ to $C_{30}$ alcohols; alcohol ethers containing 1 to 30 carbon atoms; and alkanes of the formula $H-(CH_2)n-H$ wherein n is 5 to 30. Examples of such materials include 2-ethylhexyl oxystearate; arachidyl propionate; 2-ethylhexyl adipate; isopropyl myristate; stearyl alcohol; propylene glycol; propionic acid; stearic acid; polyoxypropylene cetyl alcohol; polyoxypropylene lanolin alcohol; Carbowax" 300; petroleum jelly; mineral oil; aliphatic hydrocarbons such as mineral spirits; lanolin and lanolin derivatives such as acetylated lanolin and isopropyl lanolate.

Sunscreens are evaluated according to their ability to slow the erythema or sunburn resulting from the exposure of skin to ultraviolet light between about 290–320 nanometers (the UV-B region). This is accomplished by absorbing damaging radiation before the radiation contacts the skin surface. Para-aminobenzoic acid derivatives and cinnamates such as octyl methoxycinnamate are examples of preferable and commercially employed categories of sunscreen active compounds. UV-A region agents capable of absorbing ultraviolet light in the range of 320–400 nanometers are also useful in accordance with the present invention including benzophenones and materials such butyl methoxy dibenzoylmethane. Some additional examples of sunscreen chemicals which may be employed in accordance with the present invention are 2-ethoxyethyl p-methoxycinnamate; menthyl anthranilate; homomenthyl salicylate; glyceryl p-aminobenzoate; isobutyl p-aminobenzoate; isoamyl p-dimethylaminobenzoate;

2-hydroxy-4-methoxybenzophenone-5-sulfonic acid;

2,2'-dihydroxy-4-methoxybenzophenone;

2-hydroxy-4-methoxybenzophenone; 4-mono and 4-bis(3-hydroxypropyl)amino isomers of ethyl benzoate; and 2-ethylhexyl p-dimethylaminobenzoate.

One compound in accordance with formula (II) is the tetradecylfunctional cyclic alkylmethylpolysiloxane of the formula $(C_{14}H_{29}OMeSi)_4$ in which x is four, y is zero and z is thirteen. The durability and substantivity of this material is shown below.

EXAMPLE I

In order to illustrate the durability of the cyclic alkylmethyl polysiloxanes of the present invention in comparison to other materials described in the art, data was collected by employing a soap washing procedure that involved the measurement of substantivity on human skin. Materials that were tested included (A) mink oil, (B) a linear alkylmethyl polysiloxane having the formula

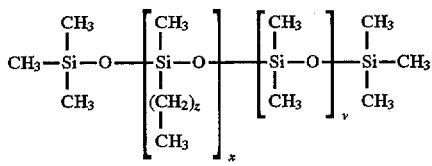

where the sum of integers x and y was six and the value of z was seventeen, and (C) a cyclic alkylmethylpolysiloxane $(C_{14}H_{29}OMeSi)_4$. Sample (C) was a material in accordance with the present invention while Samples (A) and (B) were provided for comparative purposes. Sample (B) was the Goldschmidt ABIL silicone material mentioned in the "Background" section. ABIL silicone is described by the manufacturer as polysiloxane polyalkylene copolymer and The Cosmetics, Fragrance & Toiletries Association adopted name of the material is stearyl dimethicone. ABIL is a trademark of Tho Goldschmidt AG Chemische Fabriken, Goldschmidtstrasse 100, D-4300 Essen 1. These materials are identified in the table below as samples (A), (B) and (C) respectively. Specifically the method was based on Attenuated Total Reflectance/Fourier Transform Infrared Spectrophotometric (ATR/FTIR) analysis in which skin studies were conducted and analyzed based on the reflection of energy at the prism/skin interface. Instrumentation included a NICOLET model 20DX FTIR system and a HARRICK Scientific Skin Analyzer. The ATR studies involved contact of the skin sample and prism. A hydration procedure was employed in order to increase the softness and flexibility of the skin surface which resulted in a less variable contact between the skin and prism. This hydration procedure included placing a water soaked towel against the skin test site for one minute prior to actual spectra collection. A skin test site selected was an area of about eighty square centimeters and about eight to ten milligrams of each solution tested was applied to the skin test site area in the form of a thin film using a small paint brush. From the data collected it was possible to calculate percentages of ingredients remaining on the skin following various soap wash sequences. The soap employed was a 0.5 weight percent solution of "IVORY" bar soap and a soap rub is defined as two passes over the test area with the soap solution cupped in the palm of the hand. One soap wash procedure included fifteen soap rubs and ten rinse rubs under cool running tap water. The test site was the volar forearm. The test solutions were applied to the skin test site on the forearm in the form of a mixture of the test materials dissolved in a hydrocarbon solvent such as ISOPAR G (a C10–C11 Isoparrafin sold by Exxon) or a volatile silicone fluid of low viscosity such as polydimethylcyclosiloxane which was a mixture of tetramer and pentamer and having a viscosity of about 2.5 centistokes measured at twenty-five degrees Centigrade. The solution contained ten to twenty percent by weight of the material in the solvent. The solvent was allowed to evaporate from the volar forearm region for fifteen to thirty minutes prior to the institution of the measurement procedures. The site was hydrated as noted above and the initial spectrum was collected.

A simplified test procedure is illustrated as follows. A test area on the forearm was marked and the test area was washed with the soap solution using fifteen rubs followed by rinsing with ten rubs under cool running water. Excess moisture was blotted from the forearm with a towel. After one minute the skin was hydrated for one minute using a towel saturated with water which was held loosely over the test area. Excess moisture was blotted and at the end of about fifteen to thirty seconds a background scan was run. The test mixture was applied to the skin test area and the solvent allowed to evaporate. The skin was again hydrated for one minute and excess moisture was blotted off. After thirty seconds a scan was run of the test area which represented an Initial Condition. The test area was washed with the soap solution using fifteen rubs followed by ten rinses and the excess moisture was blotted off. After one minute the skin was hydrated for one minute, blotted and at the end of about fifteen to thirty seconds a scan was run of the test area which represented a First Soap Wash Condition. Similar steps were repeated for second, third, fourth and fifth soap wash conditions. Baselines for infrared bands were defined and band heights were measured. The percent ingredient remaining on the skin was calculated using these data.

Table I indicates the results obtained by following the preceding procedure and shows that the amount of the cyclic alkylmethyl polysiloxane (C) on the skin following the fifth wash was six times the amount of mink oil (A) and double the amount of the Goldscmidt ABIL silicone described hereinabove (B). Thus the substantivity of the cyclic alkylmethyl polysiloxane for skin is substantial and unexpectedly much greater than the compounds described in the art.

TABLE I

| | Percent Remaining on Skin After Wash | | |
|---|---|---|---|
| Wash No. | Sample (A) | Sample (B) | Sample (C) |
| 1 | 23 | 43 | 53 |
| 2 | 9 | 37 | 45 |
| 3 | 6 | 24 | 39 |
| 4 | 3 | 22 | 37 |
| 5 | 5 | 17 | 32 |

EXAMPLE II

The procedure employed to collect the data shown in Table I was repeated in order to compare the cyclic alkylmethylsiloxanes of the present invention with U.S. Pat. No. 4,784,844 and U.S. Pat. No. 5,002,762 mentioned in the "Background" section. Octyl Methoxycinnamate (sold by Givaudan as Parsol MCX), a conventional sunscreen, was used for comparative purposes and as a component in a skin care formulation applied to the skin to test the ability of certain alkylmethylsiloxanes to improve the substantivity of the skin care formulation.

Samples B, C, and D were solutions containing 20 weight percent (wt %) Parsol MCX (described hereinabove), 10 wt % silicone, and 70 wt % solvent (ISOPAR G (a C10–C11 Isoparrafin sold by Exxon)). The specific Samples contained: (A) Parsol MCX (a cinnimate sunscreen) at 20 wt % in 80 wt % ISOPAR G, (B) a mixture of Parsol MCX, ISOPAR G, and an alkylmethylpolysiloxane $(C_6H_{13}MeSiO)_4$, (C) a mixture of Parsol MCX, ISOPAR G, and a cyclic alkylmethylpolysiloxane $(C_{14}H_{29}MeSiO)_4$, and (D) a mixture of Parsol MCX, ISOPAR G, and a cyclic alkylmethylpolysiloxane $(C_{20}H_{13}MeSiO)_5$. These Samples were then tested according to the procedure of Example I described hereinabove.

Samples (C) and (D) were materials in accordance with the present invention while Samples (A) and (B) were provided for comparative purposes. Sample (A) contained no alkylmethylpolysiloxane, and the Sample (B) siloxane was of significantly lower molecular weight than Sample (C) or (D). The Sample B silicone is believed to be fairly representative of the compositions taught in both U.S. Pat. No. 4,784,844 and U.S. Pat. No. 5,002,762 mentioned hereinabove. These materials are identified in Table II below as samples (A), (B), (C), and (D) respectively.

Table II below describes the results obtained by following the procedure of Example I and shows that the amount of sunscreen remaining on the skin following the third wash was substantially greater for Samples (C) and (D) when compared to the Parsol MCX solution (Sample A) and the lower molecular weight cyclic alkylmethyl polysiloxane (Sample B). As Table II below shows, the present invention retained up to 2.5 times greater the amount of sunscreen on the skin than the low molecular weight siloxanes described in the '844 patent or the '762 patent retained. In fact the lower molecular weight siloxane (Sample B) appears to have actually had a negative effect on the inherent substantivity of the sunscreen. This negative effect is indicated by Sample B having a lower percentage of sunscreen remaining on the skin than does the solution containing the sunscreen alone (Sample A).

Thus the cyclic alkylmethyl polysiloxanes of the instant invention are substantivity aids of unexpectedly greater efficacy than the compounds described in the art.

TABLE II

Percent Remaining on Skin After Wash

| Wash No. | Sample (A) | Sample (B) | Sample (C) | Sample (D) |
|---|---|---|---|---|
| 1 | 49 | 23 | 49 | 75 |
| 2 | 29 | 16 | 33 | 57 |
| 3 | 18 | 14 | 22 | 59 |

EXAMPLE III

The occlusive film forming ability of the present invention was demonstrated by conducting measurements of water loss by using an in vitro water vapor permeability test method. The rate of water loss was measured by charging stainless steel Payne permeability cups with 3 milliliters of $H_2O$ and covering the cups with collagen films spread with a thin coating of the material to be tested. The assembly is then placed in an oven at low humidity and skin temperature. Weight loss measurements are taken over time to obtain water loss rates. The results of these tests are set forth in Table III below and indicate that the alkylmethylpolysiloxanes of the present invention decrease the water vapor permeability of a substrate by the formation of an occlusive barrier on a substrate (such as skin) which retards the rate of penetration of water vapor from the substrate through the film. Samples A, B, and C were all tested at 100 weight percent. Experimentation has demonstrated a direct relationship between the ability of materials to decrease water vapor permeability in this test and their ability to reduce transepidermal water loss in vivo.

TABLE III

In Vitro Water Vapor Permeability (WVP) of Alkylmethyl Polysiloxanes

| Material | Water Loss Rate (g/m²/h) |
|---|---|
| Sample A | 106 |
| Sample B | 89 |
| Sample C | 84 |

In Table III Sample A is a cyclic alkylsiloxane described in U.S. Pat. No. 4,784,844 and U.S. Pat. No. 5,002,762 cited hereinabove and has the formula $(C_6H_{13}MeSiO)_4$, Sample (B) is a cyclic alkylmethylsiloxane of the present invention and has the formula $(C_{14}H_{29}MeSiO)_4$, and Sample C is also a cyclic alkylmethylsiloxane of the present invention and has the formula $(C_{20}H_{41}MeSiO)_5$. It can clearly be seen from the data shown in Table III that the compositions of the present invention unexpectedly reduce water loss far more effectively than the compositions described in the above mentioned patents.

EXAMPLE IV

The occlusive film forming ability of the present invention was again demonstrated by conducting measurements of water loss by using the in vitro water vapor permeability test method described hereinabove. The amounts of cyclic alkylmethylsiloxane and solvent(a C10–C11 Isoparrafin sold by Exxon as ISOPAR G) utilized in this example along with the results of these tests are set forth in Table IV below and indicate that the alkylmethylpolysiloxanes of the present invention decrease the water vapor permeability of a substrate by the formation of an occlusive barrier on a substrate (such as skin) which retards the rate of penetration of water vapor from the substrate through the film.

TABLE IV

In Vitro Water Vapor Permeability (WVP) of Alkylmethyl Polysiloxanes

| Material | Siloxane (wt %) | Solvent | Water Loss Rate (g/m²/h) |
|---|---|---|---|
| Sample A | 5 | 95 | 132 |
|  | 25 | 75 | 135 |
|  | 50 | 50 | 133 |
|  | 75 | 25 | 133 |
| Sample B | 5 | 95 | 138 |
|  | 25 | 75 | 137 |
|  | 50 | 50 | 134 |
|  | 75 | 25 | 124 |
| Sample C | 5 | 95 | 142 |
|  | 25 | 75 | 134 |
|  | 30 | 70 | 120 |
|  | 40 | 60 | 47 |
|  | 50 | 50 | 54 |
|  | 75 | 25 | 45 |
| Untreated Collagen |  |  | 124 |
| Control | 0 | 100 | 133–145 |

In Table IV Sample A is a cyclic alkylsiloxane described in U.S. Pat. No. 4,784,844 and U.S. Pat. No. 5,002,762 cited hereinabove and has the formula $(C_6H_{13}MeSiO)_4$, Sample (B) is a cyclic alkylmethylsiloxane of the present invention and has the formula $(C_{14}H_{29}MeSiO)_4$, and Sample C is also a cyclic alkylmethylsiloxane of the present invention and has the formula $(C_{20}H_{41}MeSiO)_5$. It can clearly be seen from the data shown in Table III that the compositions of the present invention unexpectedly reduce water loss far more effectively than the compositions described in the above mentioned patents.

EXAMPLE V

The procedure employed to collect the data shown in Table I and Table II was again repeated in order to show the substantivity of the present invention at varying concentrations. Octyl Methoxycinnamate (sold by Givaudan as Parsol MCX), a conventional sunscreen, was used for comparative purposes and as a component in a skin care formulation applied to the skin to test the ability of certain alkylmethylsiloxanes to improve the substantivity of the skin care formulation.

The materials that were tested were solutions containing Parsol MCX (described hereinabove), silicone, and solvent (ISOPAR G (a C10–C11 Isoparrafin sold by Exxon)). The amounts of each component are reported in Table V along with the results of the tests performed. The silicone tested in this Example was an alkylmethylpolysiloxane ($C_{20}H_{41}MeSiO)_5$. These Samples were then tested according to the procedure of Example I described hereinabove. All amounts in Table V are reported as weight percent (wt %).

Table V below describes the results obtained by following the procedure of Example I and shows that the amount of sunscreen remaining on the skin following the third wash was substantially greater for Samples that contained an alkylmethylsiloxane of the present invention as compared to those that contained no silicone component.

TABLE V

SUBSTANTIVITY

| Parsol MCX (wt %) | Siloxane (wt %) | Solvent (wt %) | % Remaining After Wash 3 |
|---|---|---|---|
| 10 | 0 | 90 | 39 |
| 20 | 0 | 80 | 20 |
| 5 | 0 | 95 | 33 |
| 20 | 10 | 70 | 59 |
| 20 | 5 | 75 | 47 |
| 10 | 10 | 80 | 56 |
| 10 | 5 | 85 | 44 |
| 10 | 2 | 88 | 46 |
| 10 | 1 | 89 | 60 |
| 5 | 1 | 94 | 41 |

The following examples illustrate the method of making the cyclic alkylmethylsiloxanes of the present invention.

EXAMPLE VI

Synthesis of Cycloalkylmethylsiloxanes

Approximately 115 grams (1 mole) of $MeHSiCl_2$ dissolved in 120 grams of toluene was added to a flask containing 500 grams of de-ionized water which was rapidly stirred in order to achieve good mixing during the addition. The products of this hydrolysis reaction were two incompatible layers. The upper layer was approximately 180 grams containing 60 grams of $(MeHSiO)x$ cyclosiloxanes with the value of x ranging from 4 to 7 dissolved in toluene (33% silicone), while the lower layer was approximately 570 grams of 12% HCl in water.

The two layers were separated and the toluene layer was washed to remove residual acid. The toluene layer was then treated with anhydrous calcium carbonate to remove any residual acid as well as water. This material was then distilled to separate the toluene, $(MeHSiO)_4$ and $(MeHSiO)_5$. Higher molecular weight cyclosiloxanes were not distilled. These can be recycled in the hydrolysis process. Approximately 25 grams (83% total yield) of each of $(MeHSiO)_4$ and $(MeHSiO)_5$ were obtained. The products were identified by analytical comparison (Gas Chromatography and Mass Spectrometry) with authentic standards.

To a mixture of 206 grams (1.05 mole) of tetradecene and 1.0 gram of 0.5% platinum on carbon heated at 100° C. without agitation was added dropwise 60 grams (0.25 mole) of pure $(MeHSiO)_4$ over a period of one hour. After complete addition of the cyclosiloxane hydride, the mixture was heated to 100° C. for two hours, cooled to 40° C. and filtered. The product $(C_{14}H_{29}MeSiO)_4$ was allowed to cool to room temperature. The product was a wax with a softening point of 27° C.

EXAMPLE VI-A

Synthesis of Cyclo(alkylmethyl-dimethylsiloxanes)

Approximately 115 grams (1 mole) of $MeHSiCl_2$ and 1161 grams (9 moles) of $Me_2SiCl_2$ dissolved in 1500 grams of toluene were added to a flask containing 5000 grams of de-ionized water, which was rapidly stirred in order to achieve good mixing during the addition. The products of this hydrolysis reaction were two incompatible layers. The upper layer was approximately 2225 grams containing 725 grams of cyclosiloxanes dissolved in toluene (33% silicone), while the lower layer was approximately 5700 grams of 13% HCl in water.

The two layers were separated and the toluene layer was washed to remove residual acid. The toluene layer was then treated with anhydrous calcium carbonate to remove any residual acid as well as water. This material was then distilled to separate the toluene and the cyclosiloxanes. After removal of the toluene, the cyclosiloxanes were seperated by distillation in the following order:

| | | |
|---|---|---|
| a) $(Me_2SiO)_3(MeHSiO)_1$ | — | 100 grams (0.35 mole) |
| b) $(Me_2SiO)_4$ | — | 160 grams (0.54 mole) |
| c) $(Me_2SiO)_4(MeHSiO)_1$ | — | 144 grams (0.40 mole) |
| d) $(Me_2SiO)_5$ | — | 150 grams (0.40 mole) |
| e) $(Me_2SiO)_5(MeHSiO)_1$ | — | 60 grams (0.14 mole) |
| f) $(Me_2SiO)_6$ | — | 40 grams (0.09 mole) |

No further materials were distilled and the siloxane residue was 75 grams. This material can be recycled in the hydrolysis process. The above materials were identified by Gas Chromatography and Mass Spectrometry.

To a mixture of 80 grams (0.315 mole) of 1-octadecene and 1.0 gram of 0.5% platinum on carbon heated at 100° C. without agitation was added dropwise a mixture of 100 grams (0.30 equivalents of Si—H) of 40 wt. % $(Me_2SiO)_3(MeHSiO)_1$, 45 wt. % $(Me_2SiO)_4(MeHSiO)_1$ and 15 wt. % $(Me_2SiO)_5(MeHSiO)_1$ over a period of one hour. After complete addition of the cyclosiloxane hydride mixture, the resultant mixture was heated at 100° C. for an additional two hours, cooled and filtered. The product, a mixture of $(C_{18}H_{37}MeSiO)_1(Me_2SiO)_{3-5}$ cyclosiloxanes was a clear, colorless, odorless liquid.

EXAMPLE VI-B

The method described in Example IV-A hereinabove was used to produce the cyclosiloxanes in this example.

To a mixture of 155 grams (0.615 mole) of 1-octadecene and 1 gram of 0.5% platinum on carbon heated to 100° C. without agitation was added dropwise a mixture of 100 grams (0.585 equivalents of Si—H) of an average composition of (MeHSiO)$_2$(Me$_2$SiO)$_{2-4}$ cyclosiloxanes over a period of one hour. After complete addition of the cyclosiloxane hydride mixture, the mixture was heated at 100° C. for an additional two hours, cooled and filtered. The product, a mixture of an average composition of (C$_{18}$H$_{37}$MeSiO)$_2$ (Me$_2$SiO)$_{2-4}$ cyclosiloxanes was a white, odorless wax with a softening point of approximately 25° C.

It should be apparent from the foregoing that many other variations and modifications may be made in the compounds, compositions and methods described herein without departing substantially from the essential features and concepts of the present invention. Accordingly it should be clearly understood that the forms of the invention described herein are exemplary only and are not intended as limitations on the scope of the present invention as defined in the appended claims.

That which is claimed is:

1. A method of treating human skin to decrease transepidermal water loss by applying to the skin a film forming conditioning formulation comprising an effective amount of a non-volatile alkylmethyl cyclic polysiloxane copolymer having the formula

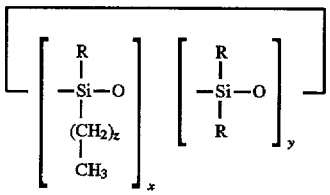

in which x and y are integers the sum of which is four, five, or six provided that x and y cannot be zero; z is an integer having a value of eleven to about twenty-nine; and R is an alkyl group having one to six carbon atoms.

2. A method of treating human skin to decrease transepidermal water loss by applying to the skin a film forming conditioning formulation comprising an effective amount of a non-volatile alkylmethyl cyclic polysiloxane copolymer having the formula

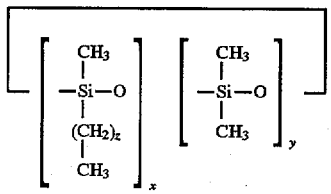

in which x and y are integers the sum of which is four, five, or six provided that x and y cannot be zero, and z is an integer having a value of eleven to about twenty-nine.

3. The method of claim 2 in which x is one, y is three, four, or five, and z is eleven to twenty-nine.

4. The method of claim 2 in which x is two, y is two, three, or four, and z is eleven to twenty-nine.

5. The method of claim 2 in which x is three, y is one, two, or three, and z is eleven to twenty-nine.

6. The method of claim 2 in which x is four, y is one or two, and z is eleven to twenty-nine.

7. The method of claim 2 in which x is five, y is one, and z is eleven to twenty-nine.

8. The method of claim 2 in which the formulation is applied to the skin in the form of a solution of the cyclic alkylmethyl polysiloxane copolymer dissolved in a volatile solvent selected from the group consisting of aliphatic hydrocarbons, aliphatic alcohols, aliphatic esters, low viscosity silicone fluids, and cyclic polysiloxanes.

9. A film forming conditioning formulation for the treatment of human skin to decrease transepidermal water loss from the skin comprising an effective amount of a non-volatile alkylmethyl cyclic polysiloxane copolymer having the formula:

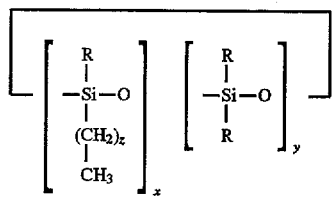

in which x and y are integers the sum of which is four, five, or six provided that x and y cannot be zero; z is an integer having a value of eleven to about twenty-nine; and R is an alkyl group having from one to six carbon atoms.

10. A film forming conditioning formulation for the treatment of human skin to decrease transepidermal water loss from the skin comprising an effective amount of a non-volatile alkylmethyl cyclic polysiloxane copolymer having the formula

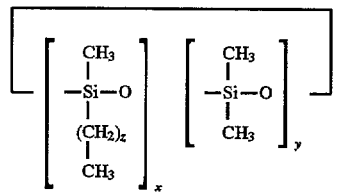

in which x and y are integers the sum of which is four, five, or six provided that x and y cannot be zero, and z is an integer having a value having a value of eleven to about twenty-nine.

11. The formulation of claim 10 in which x is one, y is three, four, or five and z is eleven to twenty-nine.

12. The formulation of claim 10 in which x is two, y is two, three, or four and z is eleven to twenty-nine.

13. The formulation of claim 10 in which x is three, y is one, two, or three and z is eleven to twenty-nine.

14. The formulation of claim 10 in which x is four, y is one or two and z is eleven to twenty-nine.

15. The formulation of claim 10 in which x is five, y is one, and z is eleven to twenty-nine.

16. The formulation of claim 10 in which the formulation is a solution of the cyclic alkylmethyl polysiloxane copolymer dissolved in a volatile solvent selected from the group consisting of aliphatic hydrocarbons, aliphatic alcohols, aliphatic esters, and low viscosity silicone fluids, and cyclic polysiloxanes.

17. A method of enhancing the substantivity of conditioning compounds on human skin comprising applying to the skin an organosilicon skin conditioning compound, the compound being applied to the skin by being dissolved in a medium, said organosilicon compound being an effective amount of a non-volatile alkylmethyl cyclic polysiloxane copolymer having the formula:

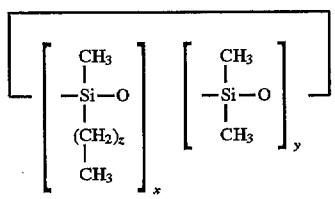

in which x and y are integers the sum of which is four, five, or six provided that x and y cannot be zero, and z is an integer having a value of eleven to about twenty-nine.

18. The method of claim 17 in which z is 11–29 and the medium is a volatile solvent selected from the group consisting of aliphatic hydrocarbons, aliphatic alcohols, aliphatic esters, and low viscosity silicone fluids, and cyclic polysiloxanes.

* * * * *